United States Patent [19]
Dias

[11] Patent Number: 5,488,955
[45] Date of Patent: *Feb. 6, 1996

[54] MAGNETOSTRICTION TRANSDUCER AND AN INTRAOPERATIVE PROBE FOR ACOUSTIC IMAGING

[75] Inventor: J. Fleming Dias, Palo Alto, Calif.

[73] Assignee: Hewlett Packard Company, Palo Alto, Calif.

[ * ] Notice: The term of this patent shall not extend beyond the expiration date of Pat. No. 5,284,148.

[21] Appl. No.: 140,902

[22] Filed: Oct. 21, 1993

Related U.S. Application Data

[63] Continuation-in-part of Ser. No. 72,828, Jun. 7, 1993, Pat. No. 5,400,788, and a continuation-in-part of Ser. No. 918,298, Jul. 22, 1992, Pat. No. 5,284,148.

[51] Int. Cl.$^6$ .......................................... A61B 8/12
[52] U.S. Cl. ................. 128/662.03; 128/662.06; 128/663.01
[58] Field of Search ........... 128/660.01, 662.03–662.04, 128/662.06, 662.01; 333/148

[56] References Cited

U.S. PATENT DOCUMENTS

| | | | |
|---|---|---|---|
| 3,922,622 | 11/1975 | Boyd et al. | 333/95 R |
| 4,077,023 | 2/1978 | Boyd et al. | 310/365 |
| 4,433,291 | 2/1984 | Yariv et al. | 324/244 |
| 4,539,846 | 9/1985 | Grossman | 73/579 |
| 4,586,381 | 5/1986 | Chamuel | 73/643 |
| 4,587,972 | 5/1986 | Morantte, Jr. | 128/660.03 |
| 4,699,009 | 10/1987 | Maslak et al. | 73/626 |
| 4,894,806 | 1/1990 | Jen et al. | 367/7 |
| 5,284,148 | 2/1994 | Dias et al. | 128/662.06 |

OTHER PUBLICATIONS

Acoustic Waves, Devices, Imaging and Analog Signal Processing, Gordon Kino, Prentice Hall, 1987.
IEEE Transactions On Microwave Theory and Techniques, vol. MTT-30, No. 4, Apr. 1982, pp. 480–484.
"Ultrasonic Thin–Wire Thermometry for Nuclear Applications", H. A. Tasman et al., American Institute of Physics, 1982, pp. 1191–1196.

Primary Examiner—Francis Jaworski

[57] ABSTRACT

This invention is a magnetostriction transducer and an intraoperative probe for acoustic imaging. The magnetostriction transducer has a coil and a magnetostriction element deposited on a portion of the acoustic waveguide that is inserted inside the coil. The magnetic field of the coil threads into the magnetostriction element and, due to the alternating magnetic field, the magnetostriction element changes its length at a rate equal to the frequency of the magnetic field. These length changes excite, among others, longitudinal waves in the core of the acoustic waveguide. The intraoperative probe has an array of acoustic waveguides bonded together. Each acoustic waveguide in the intraoperative probe has a transducer, such as a magnetostriction transducer of a piezoelectric transducer, that couples acoustic signals into the acoustic waveguides. The intraoperative probe can image the body without the extra hardware needed to rotate an acoustic waveguide by stepping an acoustic beam across the aperture of the intraoperative probe. This invention has the advantage of imaging internal organs without exposing them to danger of leakage currents.

19 Claims, 12 Drawing Sheets

MAGNETOSTRICTION TRANSDUCER AND AN INTRAOPERATIVE PROBE FOR ACOUSTIC IMAGING

CROSS-REFERENCES TO RELATED APPLICATIONS

This application is a continuation-in-part of application, filed Jun. 7, 1993, having Ser. No. 08/072828, and now U.S. Pat. No. 5,400,788 entitled "An Apparatus That Generates Acoustic Signals At Discrete Multiple Frequencies And That Couples Acoustic Signals Into A Cladded-Core Acoustic Waveguide," filed in the name of J. Fleming Dias and Hewlett E. Melton, Jr., and owned by the assignee of this application and incorporated herein by reference. Also, this application is a continuation-in-part of application, filed Jul. 22, 1992, having Ser. No. 07/918,298, entitled "Intracavity Ultrasound Diagnostic Probe Using Fiber Acoustic Waveguides," filed in the name of J. Fleming Dias and Hewlett E. Melton, Jr. and now U.S. Pat. No. 5,284,148, and owned by the assignee of this application and incorporated herein by reference.

BACKGROUND OF THE INVENTION

1. Field of the Invention

The invention relates generally to the field of ultrasound diagnostic probes and more specifically to the field of intraoperative ultrasound probes and acoustic signal transducers for ultrasound diagnostic applications.

2. Description of the Related Art

A previously known temperature probe has a low frequency magnetostriction transducer located on a plain wire (i.e., noncladded-core wire). The velocity of acoustic signals in the probe is a function of the temperature of the probe. Temperature is measured by measuring the time it takes for acoustic waves to travel from the magnetostriction transducer to the end of a calibrated temperature probe and back to the magnetostriction transducer. This device is described in "Ultrasonic Thin-Film Thermometry for Nuclear Applications" in ed. American Institute of Physics, 1982, page 1191.

A previously known magnetic field sensing device has two separate cladded-core fibers and couples light into one end of both fibers. One fiber has a magnetostriction transducer located somewhere in its middle. This transducer responds to a magnetic field by compressing the fiber and causing velocity changes and phase shifts in the light. The magnetic field is measured by comparing the phase shift of the light in one fiber with that in the other fiber, which is shielded from the magnetic field. This device is described in *Fiber Optic Sensors*, edited by Eric Udd, John Wiley & Sons, Inc. pages 382–390.

A previously known intraoperative ultrasound probe has piezoelectric transducers that the physician places directly on the artery during open heart surgery to locate the stenotic portion of an artery. The probe has miniature piezoelectric transducers configured as a phased array. These arrays operate at high frequencies, i.e., 10 to 20 MHz and require the application of a pulsed signal voltage to each piezoelectric element. These direct contact scanners are not in common use, except at the more advanced research hospitals, and they have many disadvantages. The piezoelectric transducer may emit leakage currents inside the body that can induce fibrillation when the probe images a coronary artery. Additionally, wires that connect the piezoelectric transducer to external circuitry inherently act as antennas and receive radio frequency interference present in a surgical facility.

Another disadvantage of previously known intraoperative probes is that the piezoelectric transducers configured in a phased array must be discarded after completion of a procedure to prevent transmission of disease. This is uneconomical because the piezoelectric transducers are difficult and expensive to make. It also discourages use of the most desirable transducers because they usually are more expensive. Generally, increasing the frequency of the acoustic signals improves the resolution capability of the transducer, but it also increases the expense because the operating frequency of piezoelectric transducers depends upon their thickness and the thinner the transducer, the more expensive it becomes to manufacture.

The more commonly used technique for detecting the stenotic portion of the artery during open heart surgery is palpation where surgeons literally feel with their fingers the segment of the artery that is harder than the rest. There is a widely acknowledged need to replace the palpation method with a device that is safe, economical and disposable.

For the reasons previously discussed, it would be advantageous to have an inexpensive intraoperative probe that images the arteries surrounding the heart without exposing the patient to the danger of leakage currents. Additionally, it would be desirable to have an inexpensive device for generating and coupling acoustic signals into a cladded-core acoustic waveguide that allows the acoustic waveguide to be disposable.

SUMMARY OF THE INVENTION

This invention is a magnetostriction transducer attached to a cladded-core acoustic waveguide. The magneto-striction transducer has a magnetostriction element deposited on a portion of the cladded-core acoustic waveguide and a coil positioned around the magnetostriction element. The magnetic field of the coil threads into the magnetostriction element and, due to the alternating magnetic field, the magnetostriction element changes dimensions at a rate equal to the frequency of the magnetic field. These dimensional changes excite, among others, longitudinal waves in the core of the acoustic waveguide. The acoustic waveguide may be rotated for imaging ultrasound applications, otherwise it can remain stationary and make doppler measurements of blood flow.

An advantage of this invention is safety since it generates acoustic waves for ultrasound imaging and doppler measurements outside of the body at the proximal end of the acoustic waveguide. This eliminates the danger of leakage currents that can cause fibrillation.

Another advantage of this invention is that the acoustic waveguide/catheter combination using the magnetostriction transducer is readily disposable with minimal expense. The only maneuver required is disconnection of the acoustic waveguide/catheter from the motor or other housing and connection of a replacement. The coils remain permanently attached to the motor or other housing so that magnetostriction element is the only part of the magnetostriction transducer discarded with the acoustic waveguide. Thus, this transducer is economical.

An additional advantage of this invention is that the magnetostriction transducer can generate acoustic signals at multiple frequencies with the addition of another coil (or coils) that is driven with a different frequency or frequencies. Alternatively, the same coil can be excited sequentially by signals of different frequencies.

This invention is an intraoperative probe that has a plurality of acoustic waveguides bonded together to form an array. Each acoustic waveguide has a transducer that couples acoustic signals into its proximal end. Suitable transducers include magnetostriction transducers that couple the acoustic signal to the acoustic waveguide by non-contact means and piezoelectric transducers. The magnetostriction transducer has a coil and a magnetostriction element deposited on the proximal end of the acoustic waveguide and positioned inside the coil.

When several adjacent acoustic waveguides in an intraoperative probe simultaneously transmit acoustic signals, they form an acoustic beam. Stepping the acoustic beam across the aperture of the intraoperative probe (i.e., moving the acoustic beam across the intraoperative probe by simultaneously dropping one acoustic waveguide at the trailing end of the acoustic beam and adding another at the leading end, such that the acoustic beam moves approximately a distance equal to the diameter of one acoustic waveguide) achieves ultrasound imaging without the complexity of mechanically rotating the acoustic waveguide.

This invention has the advantage of being an inexpensive tool for imaging internal organs without exposing them to the danger of leakage currents. Additionally, the high frequency acoustic signals that the acoustic waveguides transmit will result in much more precise localization and characterizations of lesions than palpation techniques allow.

DETAILED DESCRIPTION

Figure 1A:
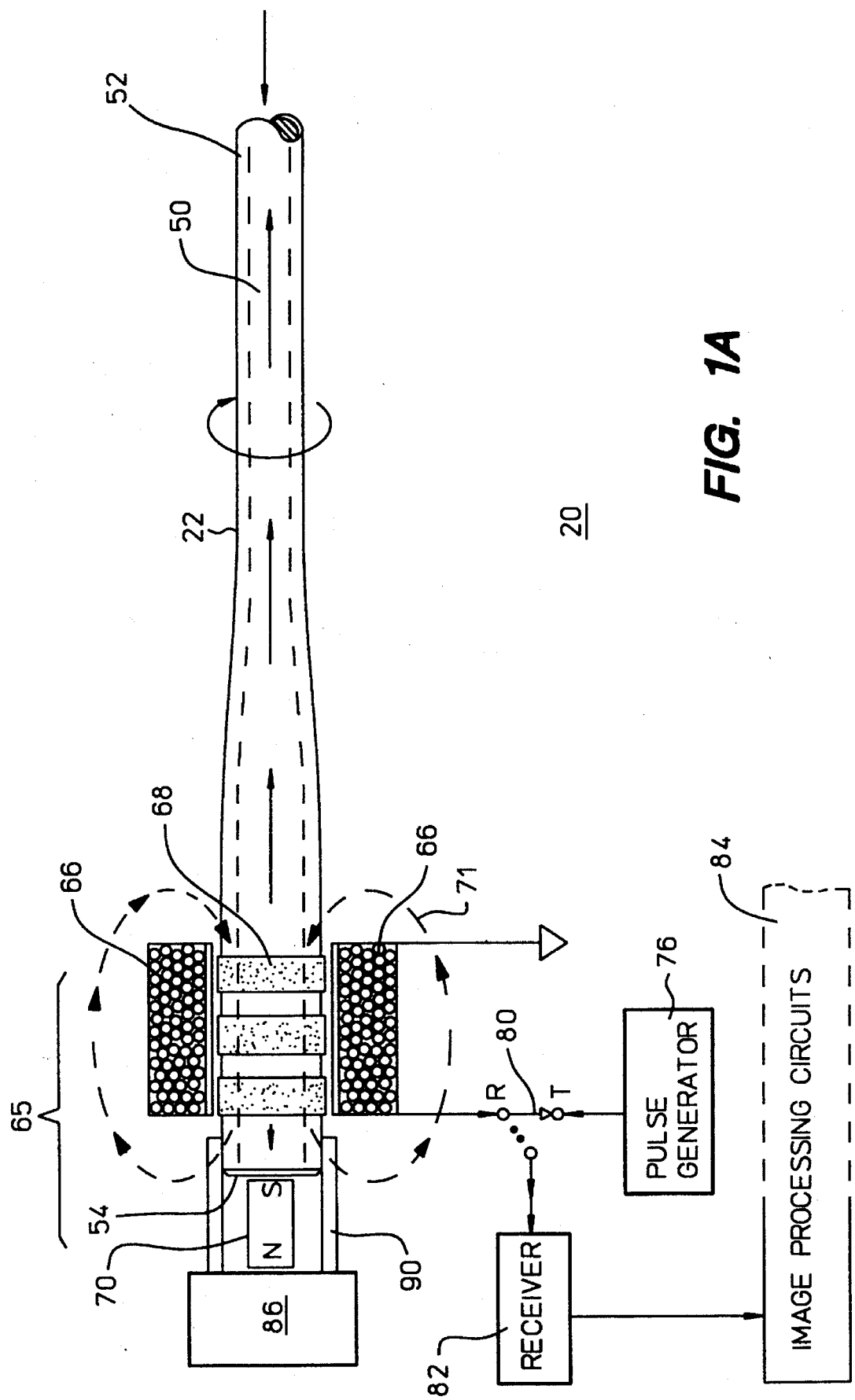
FIG. 1A shows the magnetostriction transducer coupling signals into an ultrasound imaging probe.
Figure 1B:
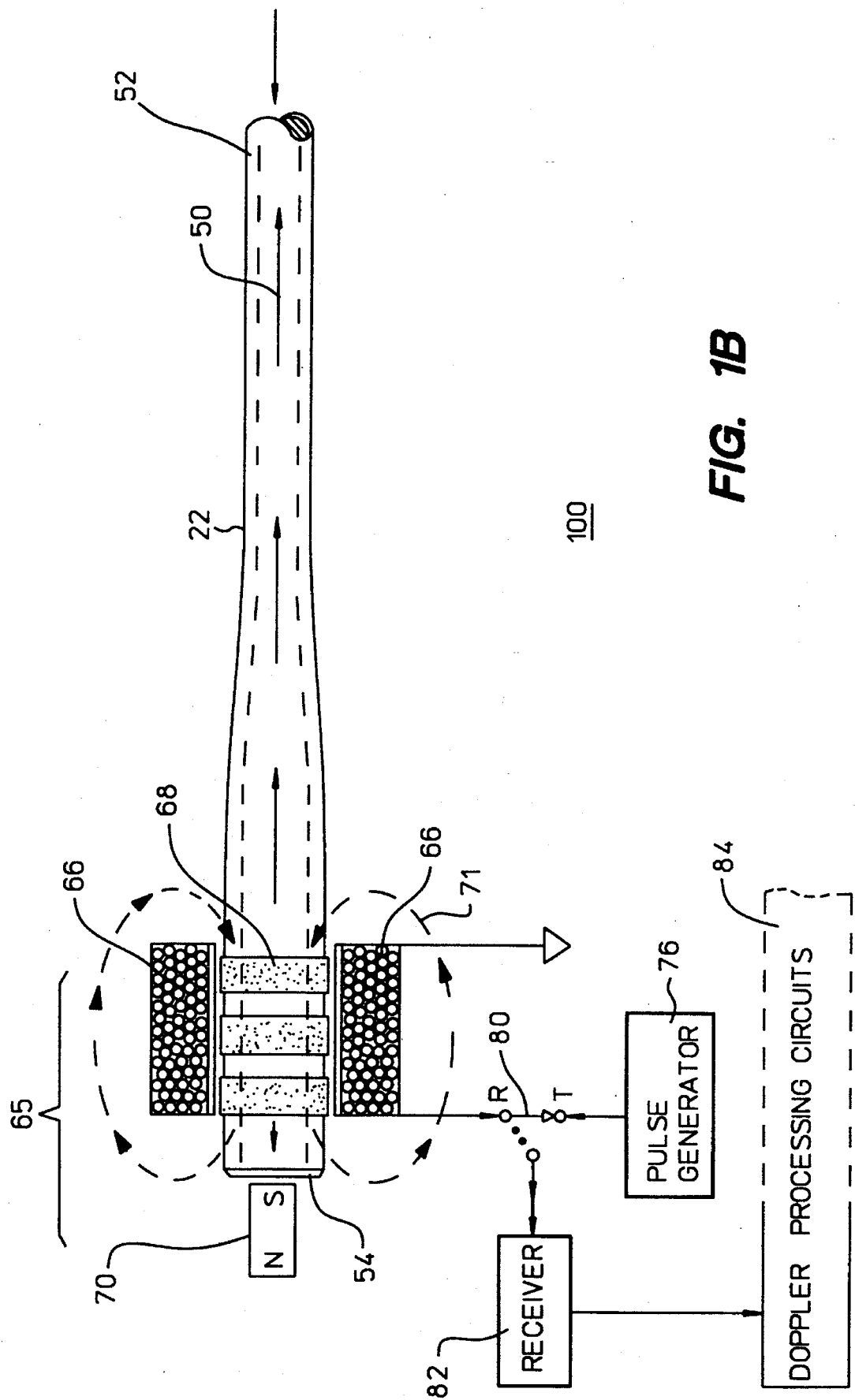
FIG. 1B shows the magnetostriction transducer coupling signals into a doppler acoustic probe.

FIG. 1A shows an imaging ultrasound probe 20 that has a magnetostriction transducer 65 attached to the proximal end of a cladded-core acoustic waveguide 22 described below, and FIG. 1B shows a doppler acoustic probe 100 with a magnetostriction transducer 65 attached to proximal end of acoustic waveguide 22. Magnetostriction transducer 65 generates acoustic signals having a frequency high enough for medical imaging and doppler measurements. The primary difference between the structure of imaging ultrasound waveguide 20 shown in FIG. 1A and doppler acoustic probe 100 shown in FIG. 1B is the motor 86 with a rotating clamp that attaches to acoustic waveguide 22 and rotates it.

Magnetostriction is the phenomenon of magneto-elastic deformation of a ferroelectric material when placed in a magnetic field. A ferromagnetic material placed along the axis of a magnetic field will change its dimensions. Magnetostriction transducer 65 has a cylindrically-shaped magnetostriction element 68 made of a ferromagnetic material such as magnetostrictive amorphous Fe-O-B ternary alloy, nickel, nickel-manganese-cobalt ferrites, iron-aluminum-cobalt (Al-Co-Fe) alloys, and other high-frequency ferrites. Standard vacuum deposition techniques, the sol-gel process, or other ceramic processing methods deposit magnetostriction element 68 around acoustic waveguide 22.

Magnetostriction transducer 65 may be attached to core 50 or to cladding 52 without departing from the scope of the invention. If magnetostriction element 68 resides on core 50, it generates the acoustic signal in the core. If magnetostriction element 68 resides on cladding 52, the acoustic signal will be generated in the cladding and travel to core 52 where it remains until it exits at the distal end of acoustic waveguide 22.

When a magnetic field permeates a magnetostriction element 68, the length (i.e., the dimension that runs parallel to the longitudinal axis of the acoustic waveguide) of the magnetostriction element 68 will change and create a pressure wave in acoustic waveguide 22. A multi-turn, high-frequency coil 66, shown in cross-section in FIGS. 1A and 1B, surrounds magnetostriction element 68 and when an alternating electric signal, $I \sin \omega t$, produced by a pulse generator 76 drives it, a magnetic field, shown by magnetic flux lines 71, having the frequency $\omega$ permeates magnetostriction element 68 and causes magnetostriction element 68 to have length vibrations parallel to the longitudinal axis of the acoustic waveguide. These vibrations excite a longitudinal acoustic signal in acoustic waveguide 22.

Figure 2:
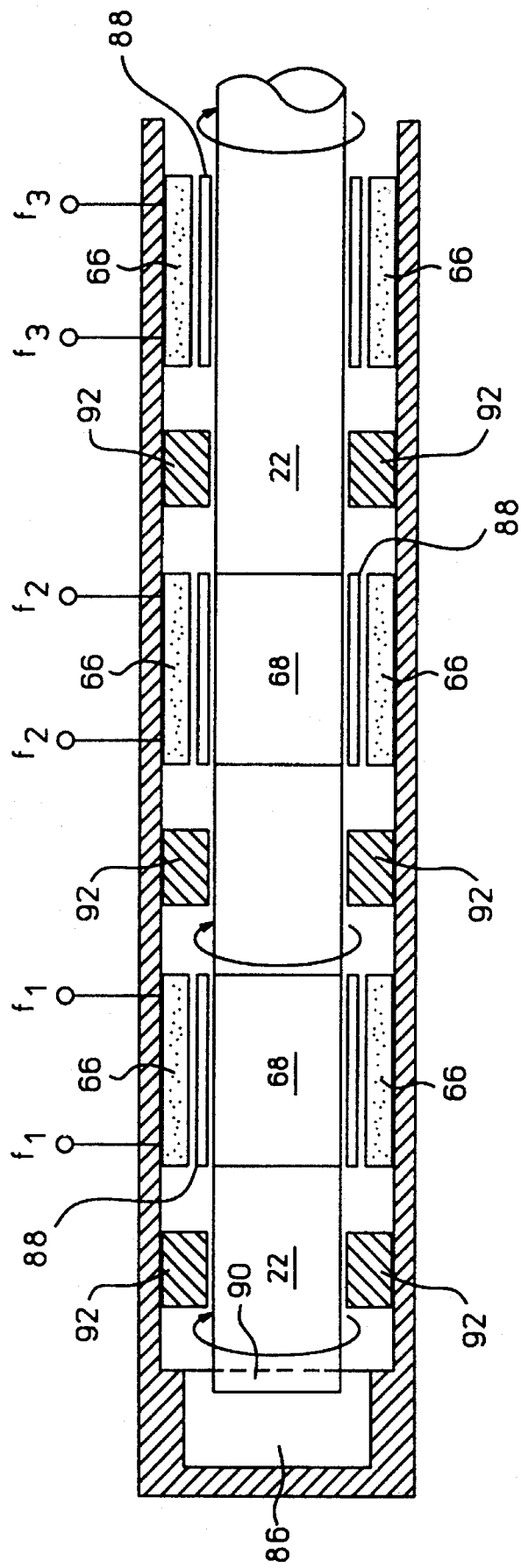
FIG. 2 shows an alternate embodiment of the ultrasound imaging probe shown in FIG. 1A with three magnetostriction transducers.
Figure 3:
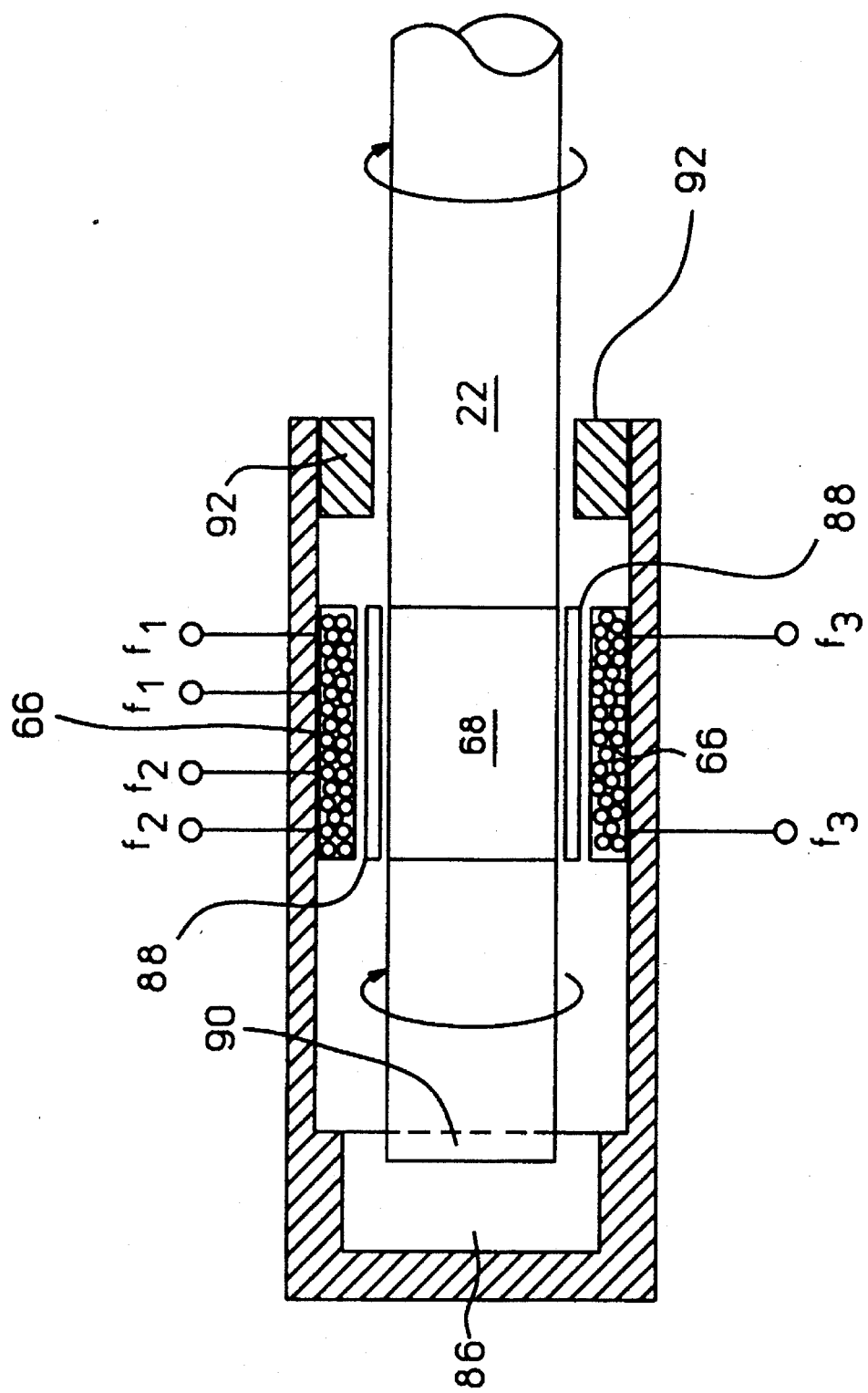
FIG. 3 shows an alternate embodiment of the magnetostriction transducer shown in FIGS. 1A, 1B, and 2 that generates three separate acoustic signals, each having a different frequency.

The acoustic signal will have the frequency $\omega$ provided an external magnetic field biases magnetostriction element 68 so that the magnetostriction material operates within the linear region of its excitation signal, I, versus magnitude of magnetic field, H, curve. In the absence of the bias field, the acoustic signal will have a large component at $2\omega$ caused by the "rectification" of the excitation signal. A permanent magnet 70 biases coil 66 and magnetostriction element 68 so magnetostriction transducer 65 operates in its linear region and responds to changes in the strength of the magnetic field with linear changes in the acoustic signal. In the preferred embodiment of the invention, permanent magnet 70 is a neodymium-iron-boron magnet, or samarium-cobalt magnet, or ferrite based ceramic magnet. FIGS. 1A and 1B show that permanent magnet 70 may be located adjacent coil 66 and acoustic waveguide 22. FIGS. 2 and 3 show an permanent magnet 88 that has a cylindrical shape so that it fits between acoustic waveguide 22 and cylindrically-shaped coil 66.

FIGS. 1A and 1B show magnetostriction element 68 deposited in bands to further increase the efficiency of transducer 65. The bands can be stacked one on top of another and properly isolated by a dielectric layer. The length of each band should equal one-half a wavelength of the magnetic excitation signal created by coil 66 so that the band resonates in its length dimension at the frequency of the excitation signal, and this increases the magneto-acoustic efficiency of magnetostriction transducer 65.

FIGS. 1A and 1B show circuitry that controls the transmission of signals flowing to and from the magnetostriction transducer 65. When switch 80 is in the "T" (i.e, transmit) position it connects pulse generator 76 to magnetostriction transducer 65 so that it generates acoustic signals in acoustic waveguide 22. These acoustic signals propagate through the waveguide to the distal end, reflect off body tissue, and reenter acoustic waveguide 22. Approximately at this time, switch 80 moves to the "R" (receive) position so that it connects the output of magnetostriction transducer 65 to receiver 82 for longer than the time required for an acoustic signal to travel to the imaging site and reflect back from the imaging site.

The reflected acoustic signal propagates back through acoustic waveguide 22 as a longitudinal mode signal. When it reaches the vicinity of the magnetostrictive transducer, the longitudinal mode signal couples acoustically with the magnetostrictive material. In the presence of a magnetic field, a voltage is generated in the coil through the magnetoelastic effect. This voltage is proportional to the magnitude of the reflected acoustic signal.

Receiver 82, in FIG. 1A, prepares the output signal of magnetostriction transducer 65 for an image processing circuitry 84 that allows a CRT 86 to display it. A control system (not shown) controls switch 80. Receiver 82, in FIG. 1B, prepares the output signal of the magnetostriction transducer 65 for Doppler shift velocity measurements made by Doppler processing circuits 84. FIG. 2 shows a rotating imaging acoustic waveguide 22 with three magnetostriction transducers 65 creating acoustic signals of three different frequencies for ultrasound imaging. Magnetostriction transducers 65 are identical with those shown in FIGS. 1A and 1B. They have a magnetostriction element 68 deposited on acoustic waveguide 22 and a coil 66 positioned around magnetostriction element 68. In this embodiment, permanent magnet 88 that biases magnetostriction transducer 65 into its linear operation range resides concentrically with acoustic waveguide 22 and coil 66. Sleeve bearings 92 support the rotating acoustic waveguide 22.

FIG. 3 shows an alternate embodiment of a rotating acoustic waveguide 22 with magnetostriction transducer 65, which is identical with that shown in FIG. 2 with the exception that it has only one magnetostriction element 68 and one permanent magnet 88, since coil 66 has three different windings and produces magnetic fields at three different frequencies.

One advantage of magnetostriction transducer 65 shown in FIGS. 1A, 1B, 2, and 3 is that acoustic waveguide 22 and its catheter (not shown) can be easily and inexpensively replaced since the only part of the magnetostriction transducer 65 attached to acoustic waveguide 22 is magnetostriction element 68, which could be made inexpensively. Coil 66 attaches to the motor housing or some other permanent hardware and it can be reused by inserting another acoustic waveguide with a magnetostriction element 68 inside it. Acoustic waveguide 22 is replaced by disconnecting it from the motor or other permanent housing and replacing it with another acoustic waveguide 22 having magnetostriction elements 68.

Figure 4:
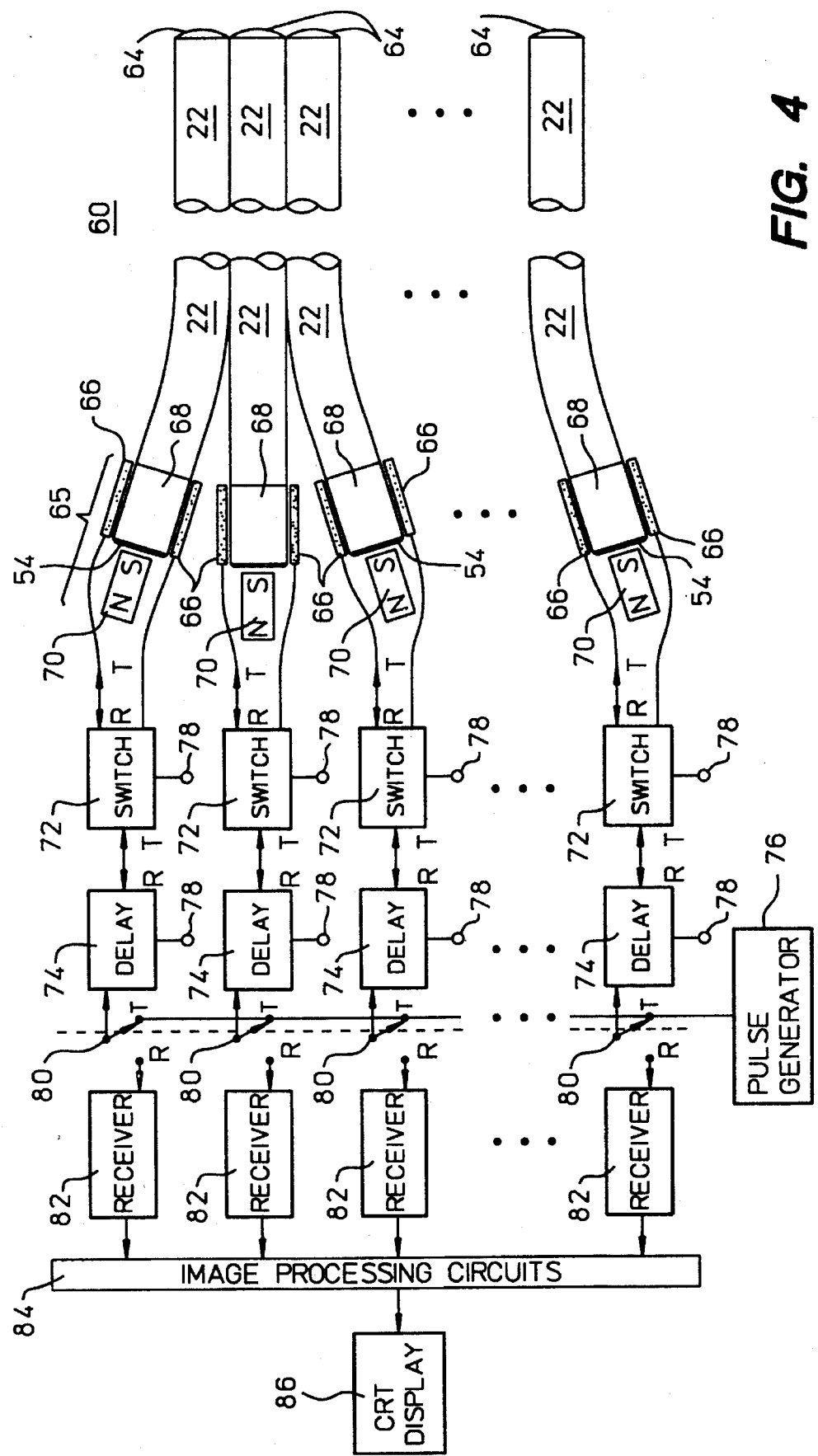
FIG. 4 shows the preferred embodiment of the intraoperative probe, configured as a linear array, that has the magnetostriction transducer shown in FIGS. 1A, 1B, and 2.
Figure 6A:
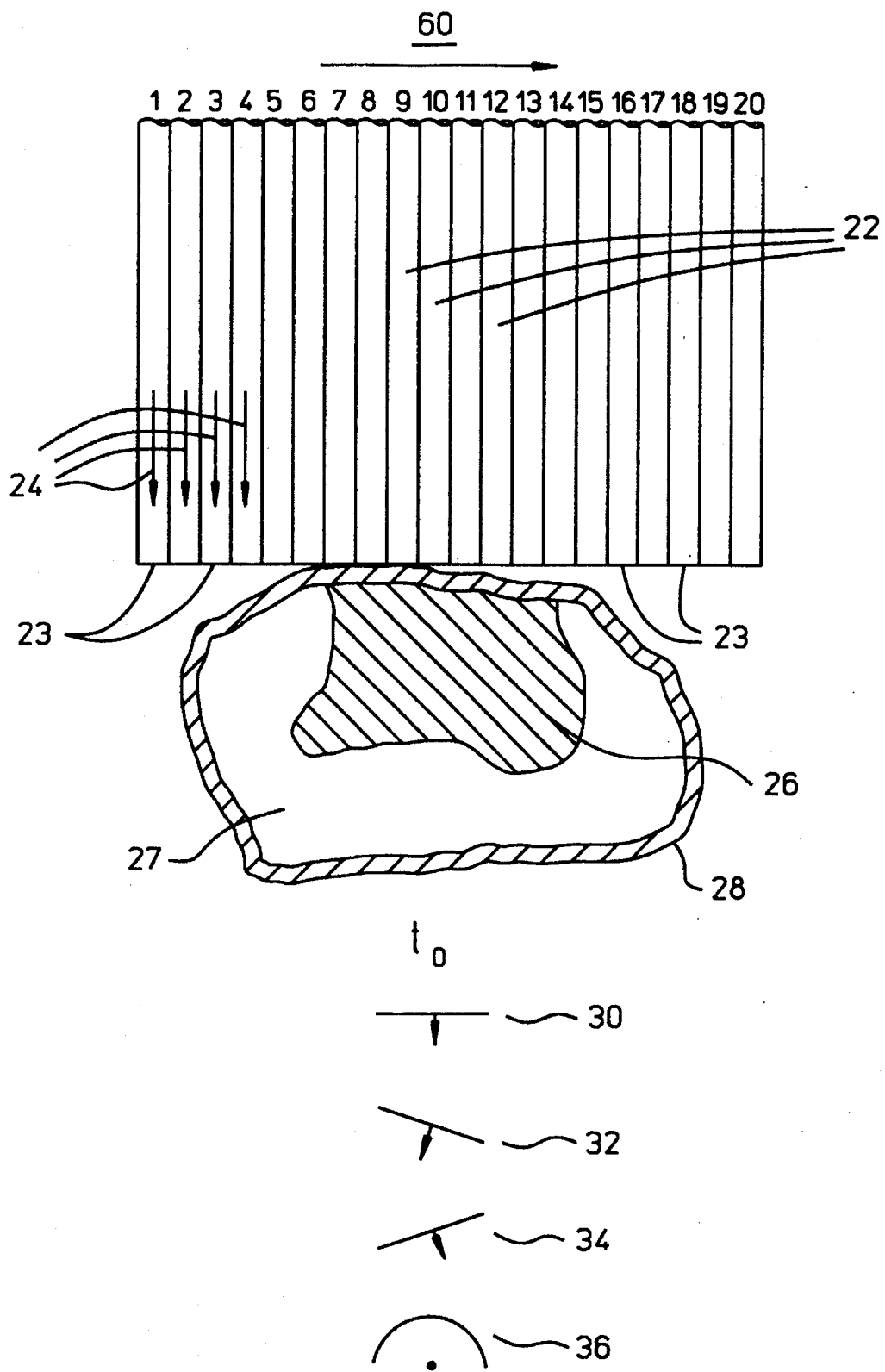
FIGS. 6A–6C show the acoustic beam walking across the intraoperative probe, shown in FIG. 4, to image a partially occluded artery shown in cross-section.
Figure 6B:
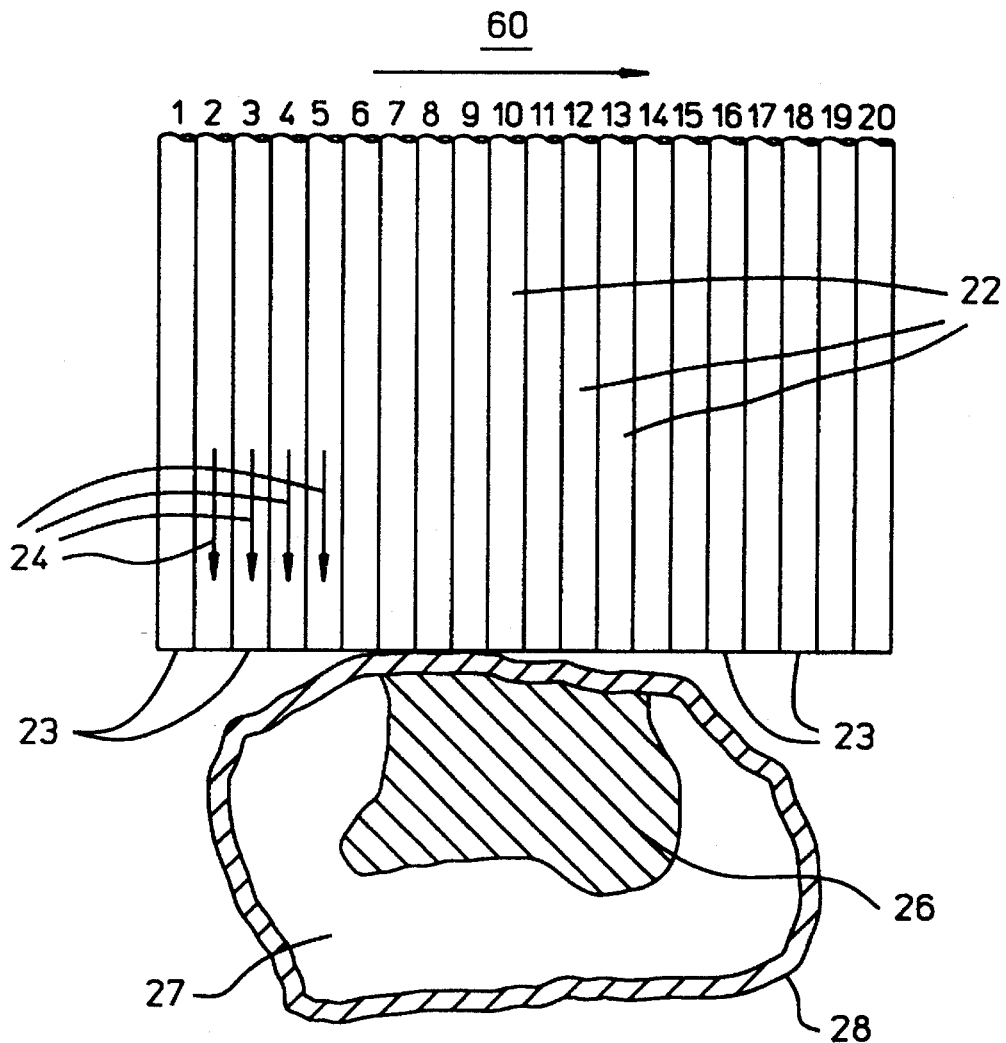
Figure 6C:
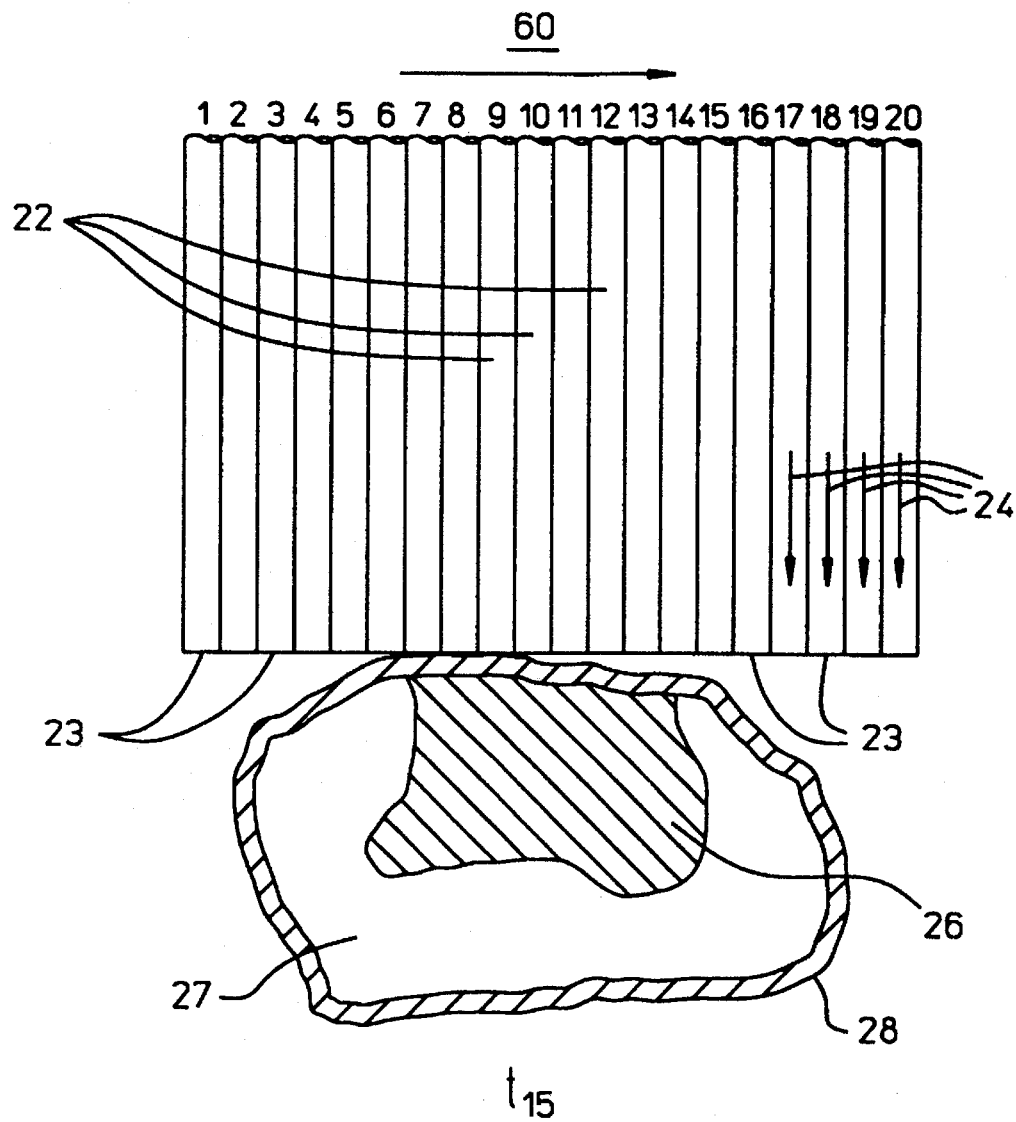

FIG. 4 shows the preferred embodiment of intraoperative probe 60 (similar to doppler acoustic probe 100 shown in FIG. 1B) for use during open heart surgery and other procedures that expose the arteries. During open heart surgery intraoperative probe 60, images arteries of the heart so that the physicians can precisely locate and characterize the occlusions of the arteries. FIGS. 6A–6C show intraoperative probe 60 imaging an artery having an artery wall 28 with an occlusion 26 partially blocking lumen 27 of the artery.

The preferred embodiment of intraoperative probe 60, shown in FIG. 4, has twenty acoustic waveguides 22 bonded with an epoxy, such as Hysol, to form an array. Each acoustic waveguide 22 has a diameter of 350 μm so that intraoperative probe 60 has a width of approximately 1 cm (e.g., approximately 700 μm of fiber and approximately 300 μm of epoxy), which is wider than the arteries. Acoustic waveguides 22 are cladded-core fibers described by C. K. Jen in a paper entitled "Similarities and Difference Between Fiber Acoustics and Fiber Optics" in the IEEE Ultrasonics Symposium, 1985 and other cladded-core fibers such as multiple cladded-core fibers that have 2, 3, or more layers of cladding 52. In cladded-core fibers with one layer of cladding, sometimes that layer must be rather thick to prevent the signal from being perturbed when the cladding is touched. Additional layers deposited on the fiber (by vacuum deposition or other technique) make the acoustic waveguide more effective in attenuating the evanescent acoustic fields in the cladding.

In general, acoustic waveguides 22 are similar to optical fibers and have a central core 50 and an outer cladding 52 that surrounds and resides on core 50. This type of cladded-core acoustic waveguide 22 supports several modes. The mode of interest is the predominately longitudinal mode that is not strictly of a guided nature and is therefore somewhat lossy. But in medical applications, the required length of acoustic waveguide 22 is around two meters or less, and the overall loss can be tolerated. The loss can be further minimized by optimizing the physical properties of the core-cladding material. It is important to note that acoustic signals become evanescent at the core-cladding interface and so the outer surface of cladding 50 can be touched without interfering with the propagating mode, this would be especially true of waveguides with multiple claddings. Using the same reasoning, the crosstalk between adjoining acoustic waveguides 22 is minimal, even when their claddings 52 touch one another.

To obtain an acoustic waveguide 22 for the ultrasound intraoperative probe with minimum attenuation for longitudinal modes, the following must be minimized:

1. The shear wave velocity difference ε, between core 50 and cladding 52 must be much less than unity:

$$\epsilon_s = \frac{V_{SCL} - V_{SCO}}{V_{SCO}} \ll 1.$$

2. The density difference between the core 50 and cladding 52 also must be much less than unity:

$$\epsilon_p = \frac{\rho_{CL} - \rho_{CO}}{\rho_{co}} \ll 1$$

and when $\epsilon_g = \epsilon_p = 0$, the modes are tightly bound to the core and the transmission loss is minimum.

3. For the existence of the longitudinal modes, the following condition also must be satisfied.

$$\epsilon_L = \frac{V_{LCL} - V_{LCO}}{V_{LCO}} << 1$$

but $\neq 0$ where $V_{LCO}$ is the longitudinal velocity in the core.

Most multimode glass optical fibers satisfy, to some degree, the above conditions and are used in experiments involving the transmission of ultrasound pulses at high frequencies. Other materials that meet the above conditions also can be used and are included within the scope of the invention.

Each tip 23 of acoustic waveguide 22 is lapped and polished flat and lies in a plane normal to the longitudinal axis of acoustic waveguide 22. Each tip 23 has a matching layer 64 to match the acoustic impedances of acoustic waveguide 22 and the body. Tips 23 have lens 62 whenever needed. Alternatively, the tips may be shaped to achieve focusing or other beam profiles.

An acoustic transducer excites the proximal ends of acoustic waveguides 22. The preferred embodiment of the invention uses a magnetostriction transducer 65 shown in FIGS. 1A, 1B, 2, and 3 and described in previous paragraphs.

Acoustic signals generated by the oscillations of magnetostriction element 68 will travel toward the distal end 23 and toward the proximal end of acoustic waveguide 22. Those that travel to the proximal end will reflect off the proximal end and interfere with the acoustic signals traveling in the other direction, especially if they are out-of-phase with them. To eliminate this problem, the proximal ends have an acoustic absorber 67, such as a mixture of 1 micron of tungsten powder, teflon powder, and an epoxy of the Hysol type. Another way to eliminate the problem of out-of-phase reflected acoustic signals is to positioned the end of acoustic waveguide 22 so that the reflected waves are in-phase with the other acoustic waves that travel to the distal end.

Figure 5:
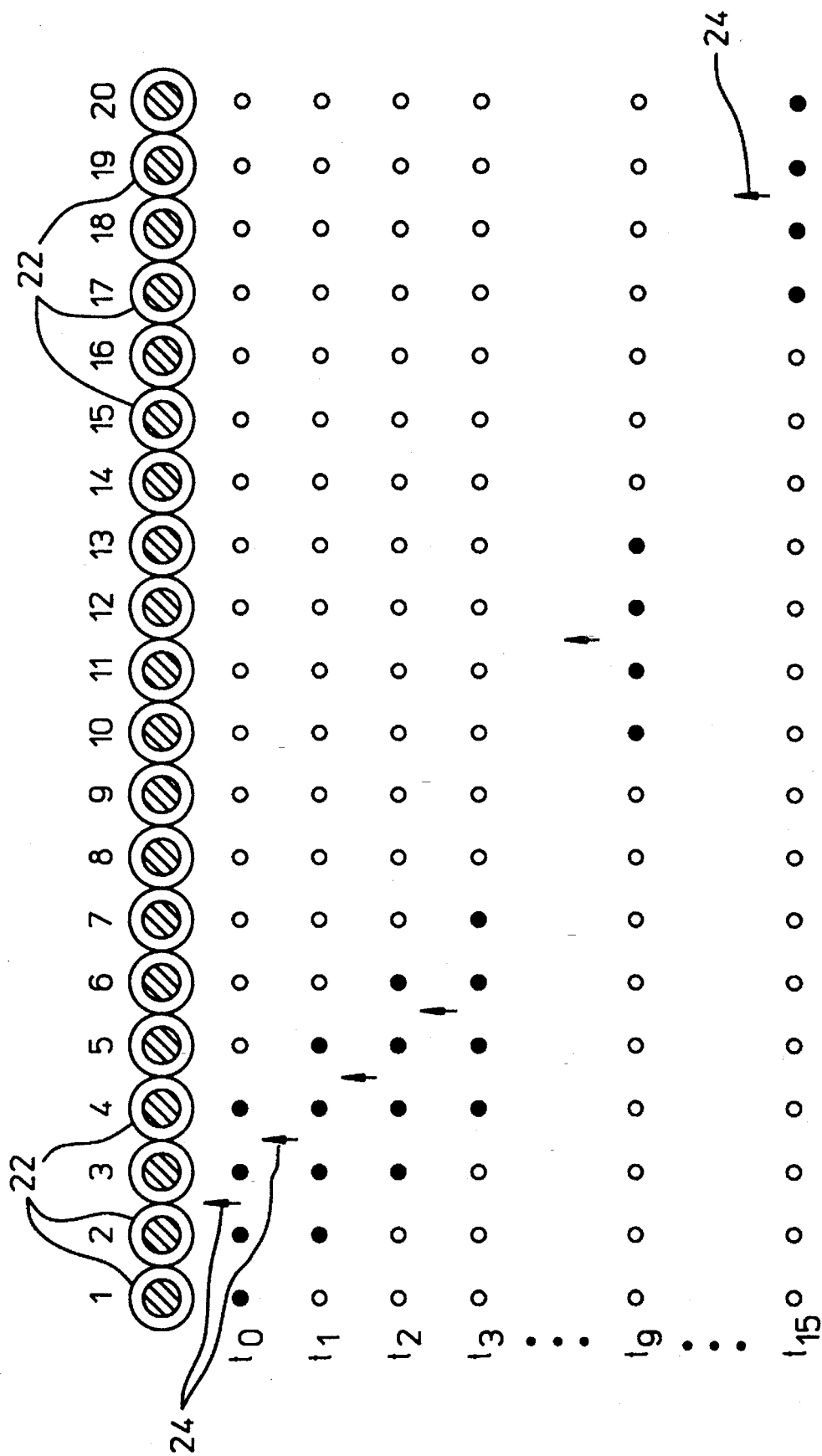
FIG. 5 is a timing diagram of the intraoperative probe shown in FIG. 4.

FIG. 5 is a timing diagram for the transmission of acoustic signals in intraoperative probe 60. Acoustic waveguides 22 of intraoperative probe 60 are positioned across the top and the left hand column contains the timing intervals. In the preferred embodiment, there are 16 separate timing intervals, $t_0, t_1, t_2, \ldots t_{15}$. Each filled-in dot 25 indicates that the corresponding acoustic waveguide 22 transmits an acoustic signal during that timing interval and an empty dot 29 indicates the absence of an acoustic signal during that timing interval.

In the preferred embodiment of the invention, four magnetostriction transducers 65, shown in FIG. 4, couple four acoustic signals into four acoustic waveguides 22 to form acoustic beam 24. These acoustic signals have the same frequency, typically somewhere between 10 and 40 megacycles. By progressively stepping the acoustic beam across the aperture of intraoperative probe 60, ultrasound imaging is achieved without the complexity of mechanically rotating the acoustic waveguides. FIGS. 6A–6C show acoustic beam 24 stepping across intraoperative probe 60 to image a partially occluded artery shown in cross-section.

FIG. 6A shows that during timing interval $t_0$ acoustic waveguides 22 with the numbers 1–4 transmit acoustic beam 24. The number 1 acoustic waveguide is a lagging acoustic waveguide and the number 4 acoustic waveguide is a leading acoustic waveguide since acoustic beam 24 moves to the right across array 60. During the transition from timing interval $t_0$ to timing interval $t_1$, switches 72 disconnects the number 1 acoustic waveguide and connects the number 5 acoustic waveguide so that the number 5 acoustic waveguide transmits an acoustic signal that forms a portion of acoustic beam 24 when timing interval $t_1$ begins. Thus, as FIG. 6B shows, during time interval, $t_1$, the number 2–5 acoustic waveguides 22 transmit acoustic beam 24.

The preferred embodiment of the intraoperative probe repeats the stepping procedure during the transition between timing intervals $t_1$ and $t_2$, between timing intervals $t_2$ and $t_3$, and so on until it reaches timing interval $t_{15}$. The advantage of stepping acoustic beam 24 as described above is that ultrasound imaging can be accomplished without a motor and other extra hardware needed to rotate an acoustic waveguide.

FIG. 4 shows circuitry for controlling the operation of intraoperative probe 60 and for processing the signals received from intraoperative probe 60. This circuit configuration is very similar to that shown in FIGS. 1A and 1B. Each acoustic waveguide 22 has a switch 80 and these switches operate in unison and are digitally controlled. When switches 80 are in the "T" position, they connect pulse generator 76 to a bank of individually controlled switches 72. Switches 72 connect the output of pulse generator 76 to some or all magnetostriction transducers 65. In the preferred embodiment of the invention, switches 72 connect four magnetostriction transducers 65 to pulse generator 76 simultaneously.

After magnetostriction transducers 65 have generated acoustic signals for an appropriate amount of time, the bank of switches 80 disconnects them from pulse generator 76 and connects them to receiver 82 for at least the length of time it takes acoustic signals to travel from magnetostriction transducer 65 to the furthest imaging site plus the time it takes the reflected acoustic signal to travel from the imaging site to magnetostriction transducers 65.

The preferred embodiment of intraoperative probe 60 generates a wavefront 30, shown in FIG. 6A, since all four magnetostriction transducers 65 generate acoustic signals simultaneously. FIG. 4 shows a delay circuit 74 that can delay when pulse generator 76 drives an individual magnetostriction transducer 65. By delaying the excitation of individual magnetostriction transducers 65, the direction of the wavefront can be altered as wavefronts 32, 34, and 36 shown in FIG. 6A. The phased delays can be used to create a wavefront that focuses acoustic beam 24 on the artery or another target.

Alternate embodiments of the intraoperative probe may use piezoelectric transducers instead of magnetostriction transducers to generate the acoustic signals. When intraoperative probe 60 uses piezoelectric transducers instead of magnetostriction transducers 65, it is identical with the intraoperative probes previously described except that piezoelectric transducers replace magnetostriction transducers 65.

Figure 7:
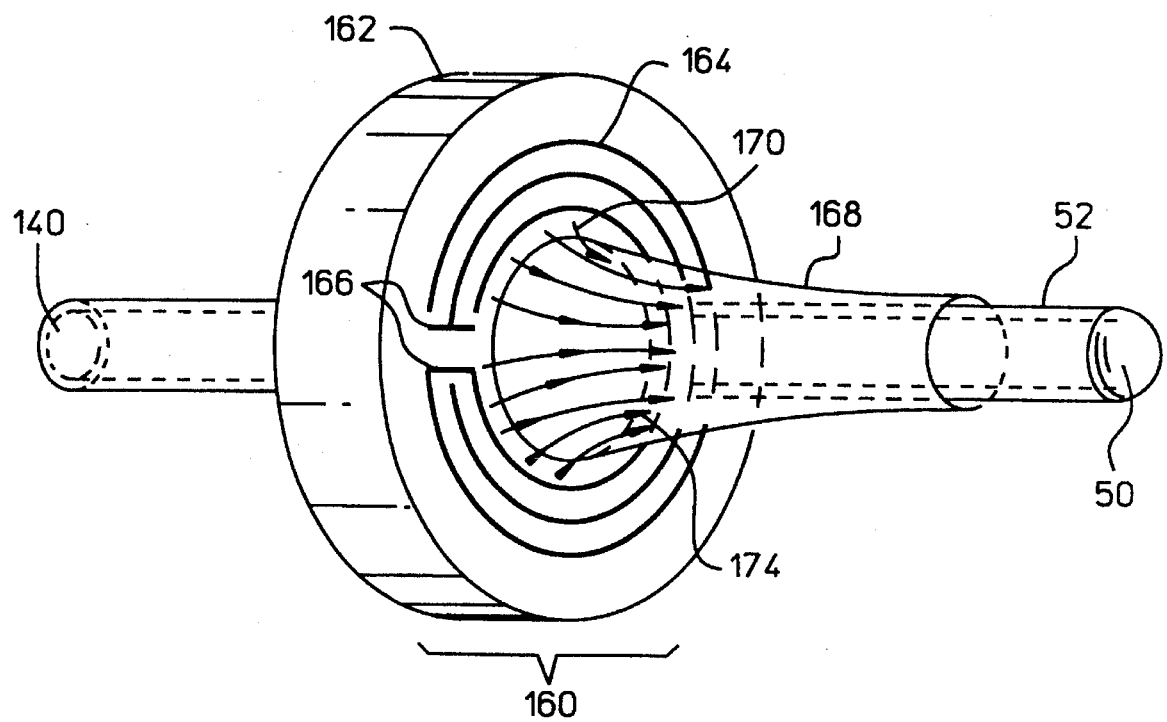
FIG. 7 shows a piezoelectric SAW transducer used in an alternate embodiment of the intraoperative probe shown in FIG. 4.
Figure 8A:
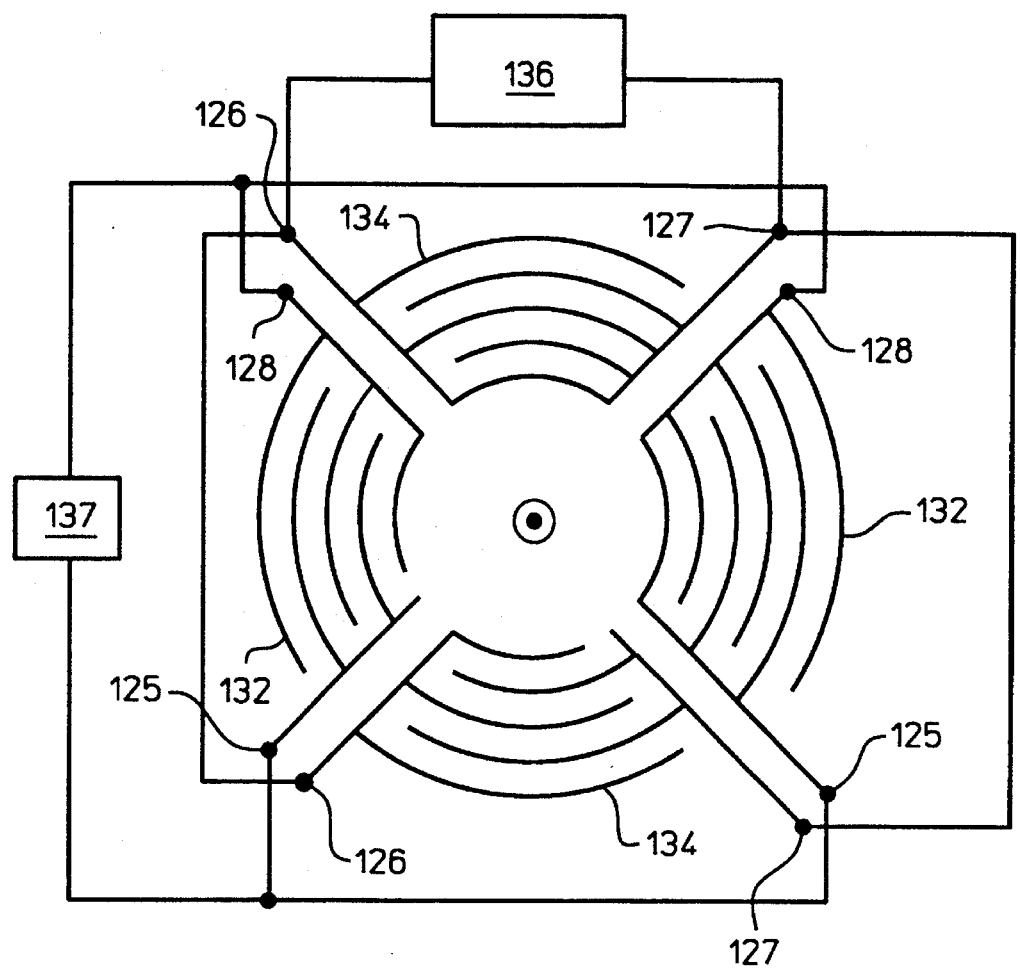
FIG. 8A and 8B show other embodiments of the curvilinear interdigital conductors that can be used in the piezoelectric SAW transducer shown in FIG. 7.
Figure 8B:
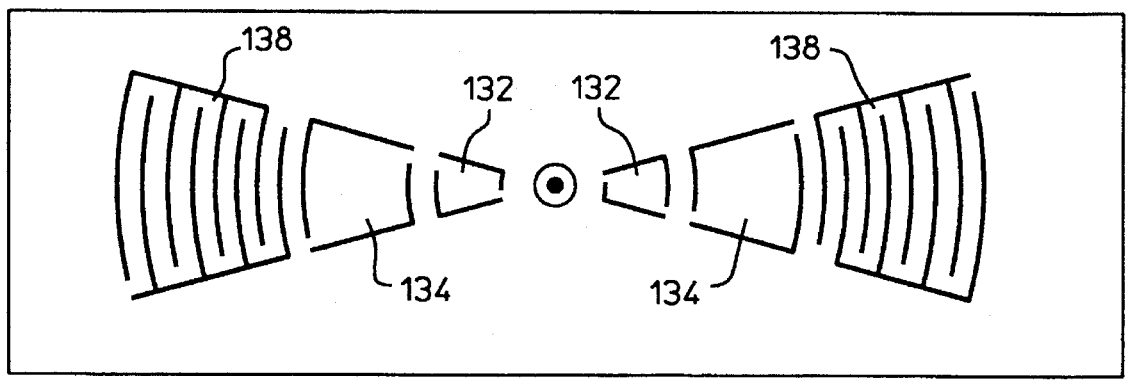

FIG. 7 shows the preferred embodiment of piezoelectric transducer 160 that generates surface acoustic waves 170 that couple into medium 168 that converts them into leaky waves 174. These leaky waves 174 pass through cladding 52 and into core 50 of acoustic waveguide 22 where the longitudinal mode predominates. The longitudinal mode of acoustic signals is preferred because fluids, like blood, do not support other waves-they only support longitudinal waves. Piezoelectric transducer 160 has a piezoelectric disc substrate 162, preferably made out of PZT, and curvilinear interdigital conductors 164 that are driven by an electric signal transmitted by wires 166 that connect to switch 72 shown in FIG. 4.

Piezoelectric transducers that generate surface acoustic waves (SAW) have the advantage of being easy to make and robust because the frequency of the acoustic signal produced depends upon the spacing of interdigital conductors 164 that standard photolithographic techniques can control. This embodiment of piezoelectric transducer generates SAW's at a single frequency. Alternate embodiments of piezoelectric transducer 160, use curvilinear conductors 132, 134, 138 shown in FIGS. 9A and 9B and generate SAW's at multiple discrete frequencies. Conductors 132, 134, 138 can have the arrangement shown in FIG. 9A or 9B.

The thickness of piezoelectric substrate 162 should be more than 100 times the wavelength of the SAW's so that they travel on the surface of piezoelectric disc 162 as arrows 170 show. SAW's become leaky longitudinal waves when the velocity of the longitudinal waves in the coupling medium, $V_L$, is less than the velocity of SAW's in the coupling medium, $V_{SW}$. The acoustic waves change their direction by an angle θ when they enter coupling medium 168. This angle is equal to $$\theta = \arcsin \frac{V_L}{V_{SW}}.$$

If the coupler is water, then θ≅43°.

Commercially available elastomers such as Sylgard, RTV, and butyl rubber satisfy this condition. This embodiment of the invention can detect reflected acoustic waves by attaching a broad band receiver 140, such as PVDF copolymer, to the core at the proximal end.

Alternate embodiments of intraoperative probe may use a piezoelectric transducer having the shape of spherical annulus or a spherical shell having a radius of curvature R with a focus point at the end of an acoustic waveguide. The piezoelectric transducers are permanently attached to an acoustic horn located between the piezoelectric transducers and the acoustic waveguide. The spherical shape and polarization of each transducer causes them to focus almost all their acoustic energy through the horn to a focal point adjacent to the core of an acoustic fiber.

Another alternate embodiment of the intraoperative probe may use a piezoelectric transducer ring in the shape of a conical annulus that wraps around a conically shaped coupling prism and couples acoustic signals into the core through the cladding. The bulk/longitudinal waves it generates travels through coupling prism, through the cladding of the acoustic waveguide, and into the core of the acoustic waveguide.

Figure 9:
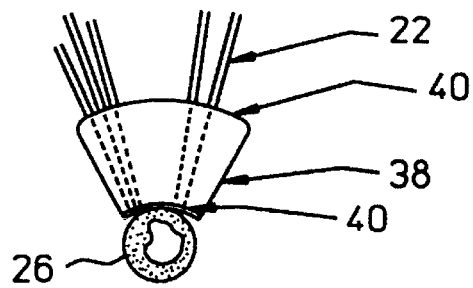
FIG. 9 shows an alternate embodiment of the invention that uses a buffer block to focus acoustic signals emitted from the intraoperative probe, shown in FIG. 4, on to the artery.

FIG. 9 shows an embodiment of the invention that focuses acoustic beam 24 onto the artery. It has a buffer block 38 of acoustically clear material placed between acoustic waveguides 22 and an arterial wall 28. Buffer block 38 has two concentric surfaces 40, 41 and acoustic waveguides 22 attached to the outer concentric surface 40 of buffer block 38. This attachment should be capable of providing optimum transmission of ultrasonic pulses from the end of acoustic waveguide 22 to buffer block 38. The pulses propagate through the block to the inner concentric surface 41 that has a matching layer. Inner concentric surface 41 contacts arterial wall 28 of the targeted artery 26

Delay circuits 74, shown in FIG. 4, can create phased delays in the acoustic signals transmitted to buffer block 38. The delays can create concentrically-shaped wavefronts that conform to the shape of an artery and image the cross-section of that artery.

Figure 10A:
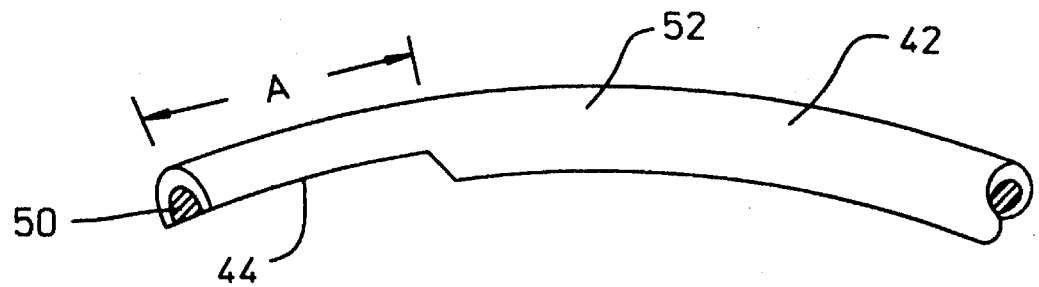
FIGS. 10A–10C show an alternate embodiment of the invention that has the distal end of the intraoperative probe, shown in FIG. 4, lapped to the core.
Figure 10B:
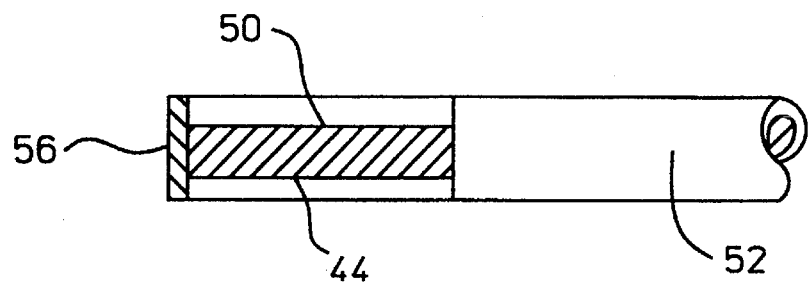
Figure 10C:
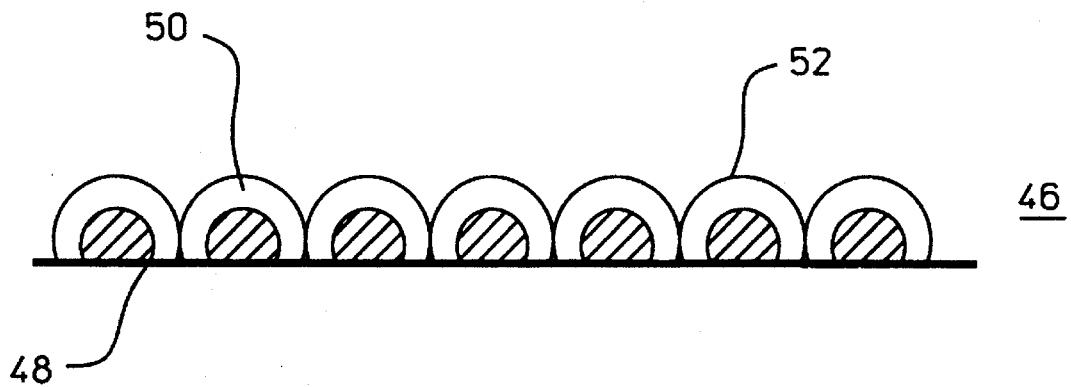

FIGS. 10A–10C show another embodiment of the intraoperative probe that has acoustic waveguides 42 with a lapped end. An exit port 44 is created at the distal end that is parallel to the longitudinal axis of acoustic waveguide 42. Since cladding 52 is lapped down to core 50, the ultrasound pulse that arrives at this end is no longer a guided mode and exits acoustic waveguide 22 here. When several of these acoustic waveguides 22 are arranged side by side with all lapped surfaces facing the same direction, the array 46 is created.

What is claimed is:

1. A magnetostriction transducer for medical use, comprising:
   A. a cladded-core acoustic waveguide means for transmitting an acoustic signal from a proximal end of the cladded-core acoustic waveguide means into a body and for transmitting a reflected acoustic signal from the body to the proximal end of the cladded-core acoustic waveguide means;
   B. a first generating means for generating a first alternating magnetic field at the proximal end of the cladded-core acoustic waveguide means; and
   C. a magnetostriction element means, attached to the proximal end of the cladded-core acoustic waveguide means, for converting the first alternating magnetic field into the acoustic signal and for coupling the acoustic signal into the proximal end of the cladded-core acoustic waveguide means, and for converting the reflected acoustic signal into a reflected alternating magnetic field.

2. The magnetostriction transducer, as in claim 1, wherein the first generating means is physically separate from the cladded-core acoustic waveguide means and further comprising a replacing means for temporarily holding the cladded-core acoustic waveguide means adjacent to the first generating means and for facilitating replacement of the cladded-core acoustic waveguide means.

3. The magnetostriction transducer, as in claim 1, wherein the first generating means further comprises:
   a coil; and
   a driving means for driving the coil with a first electric current to create the first alternating magnetic field.

4. The magnetostriction transducer, as in claim 3, further comprising a connector means for temporarily holding the cladded-core acoustic waveguide means inside the coil and for facilitating replacement of the cladded-core acoustic waveguide means.

5. The magnetostriction transducer, as in claim 1, wherein the magnetostriction element means further comprises one or more bands of magnetostriction material deposited on the cladded-core acoustic waveguide means and each band has a length equal to one-half a wavelength of the first alternating magnetic field.

6. The magnetostriction transducer, as in claim 1, further comprising a second generating means for generating a second alternating magnetic field having a second frequency, the second generating means drives the magnetostriction element means.

7. The magnetostriction transducer, as in claim 6, further comprising a second magnetostriction element means located on the cladded-core acoustic waveguide means.

8. The magnetostriction transducer, as in claim 7, wherein the second generating means further comprises:
   a second coil; and
   a second driving means for driving the second coil with a second electric current to create a second alternating magnetic field.

9. The magnetostriction transducer, as in claim 8, wherein the second magnetostriction element means further comprises a plurality of bands and each band has a length equal to one-half a wavelength of the second alternating magnetic field.

10. An intraoperative probe for acoustic imaging, comprising:

a plurality of cladded-core acoustic waveguide means for transmitting an acoustic signal from a proximal end of the cladded-core acoustic waveguide means into a body and for transmitting a reflected acoustic signal from the body to the proximal end of the cladded-core acoustic waveguide means, the plurality of cladded-core acoustic waveguide means are bonded together into an array;

a plurality of generating and coupling means, each generating and coupling means is attached to the proximal end of one cladded-core acoustic waveguide means, each for generating the acoustic signal and coupling the acoustic signal into the proximal end of the attached cladded-core acoustic waveguide means; and a means for controlling the plurality of generating and coupling means and so the acoustic signals form an acoustic beam for acoustic imaging.

11. The intraoperative probe, as in claim 10, wherein the plurality of generating and coupling means further comprises: a plurality of piezoelectric transducers, each piezoelectric transducer generates and couples the acoustic signal into the proximal end of the attached cladded-core acoustic waveguide means.

12. The intraoperative probe, as in claim 11, wherein each generating and coupling means further comprises:

a piezoelectric disc substrate attached to one cladded-core acoustic waveguide means;

one or more curvilinear conductors positioned on the piezoelectric disc substrate, curvilinear conductors generate a surface acoustic wave; and a surface acoustic wave coupler means for coupling the surface acoustic wave into the attached cladded-core acoustic waveguide means through the cladding.

13. The intraoperative probe, as in claim 10, wherein the plurality of generating and coupling means for generating and coupling is a plurality of magnetostriction transducers, each magnetostriction transducer connects to the proximal end of one cladded-core acoustic waveguide means.

14. The intraoperative probe, as in claim 13, wherein the magnetostriction transducer further comprises:

a magnetostriction element means deposited on each cladded-core acoustic waveguide means;

a coil positioned around each magnetostriction element means; and a driving means for driving the coil with an electric current.

15. The intraoperative probe, as in claim 13, further comprising a connector means for replacing the cladded-core acoustic waveguide means.

16. A method for acoustic imaging, comprising:

A. creating a high-frequency alternating magnetic field;

B. driving a magnetostriction element located on the proximal end of a cladded-core acoustic waveguide with the high-frequency alternating magnetic field;

C. generating high-frequency acoustic waves in the cladded-core acoustic waveguide;

D. transmitting the acoustic waves to a distal end of the cladded-core acoustic waveguide located inside a body;

E. receiving reflected high-frequency acoustic waves from inside the body; and

F. generating a voltage in the coil.

17. A method, as in claim 16, further comprising the steps of:

driving a coil with a high-frequency current to create the high-frequency magnetic field; and generating a reflected high-frequency voltage in the coil from the high-frequency magnetic field created by the magnetostriction element.

18. A method, as in claim 17, further comprising the step of rotating the cladded-core acoustic waveguide.

19. A method, as in claim 17, further comprising the step of stepping the high-frequency acoustic field across an aperture of an intraoperative probe.

* * * * *